United States Patent [19]

Theissen

[11] 4,029,493
[45] June 14, 1977

[54] SUBSTITUTED PHENOXYBENZONITRILES AS HERBICIDES

[75] Inventor: Robert James Theissen, Union County, N.J.

[73] Assignee: Mobil Oil Corporation, New York, N.Y.

[22] Filed: May 21, 1975

[21] Appl. No.: 579,520

Related U.S. Application Data

[60] Division of Ser. No. 335,408, Feb. 23, 1973, Pat. No. 3,923,858, which is a continuation-in-part of Ser. No. 69,959, Sept. 4, 1970, abandoned.

[52] U.S. Cl. ............................................. 71/105
[51] Int. Cl.² ........................................ A01N 9/20
[58] Field of Search .................................... 71/105

[56] References Cited
UNITED STATES PATENTS

| | | | |
|---|---|---|---|
| 3,535,365 | 10/1970 | Weinstock et al. | 260/465 |
| 3,702,862 | 11/1972 | Mine et al. | 71/105 |

FOREIGN PATENTS OR APPLICATIONS

| | | |
|---|---|---|
| 1,912,600 | 9/1969 | Germany |
| 951,651 | 3/1964 | United Kingdom |

*Primary Examiner*—Lewis Gotts
*Assistant Examiner*—Catherine L. Mills
*Attorney, Agent, or Firm*—Charles A. Huggett; Hastings S. Trigg

[57] ABSTRACT

Phenoxybenzonitriles, halo-substituted on the phenoxy ring and halo- or alkyl-substituted on the benzonitrile ring ortho to the para-cyano position, form a new class of herbicides. These substituted phenoxybenzonitriles and herbicidal compositions containing them are highly effective as pre-emergence and post-emergence herbicides, especially at low use concentrations. They are highly effective against Crabgrass, Yellow Foxtail grass and Barnyard grass, annual grass weeds which reproduce by seed. They are also highly effective against Johnson grass, a perennial grass weed which reproduces by seed and underground rhizomes, and Pigweed, an annular broadleaf weed which reproduces by seed.

5 Claims, No Drawings

SUBSTITUTED PHENOXYBENZONITRILES AS HERBICIDES

CROSS-REFERENCE TO RELATED APPLICATIONS

This is a division of application Ser. No. 335,408, filed Feb. 23, 1973 now U.S. Pat. No. 3,923,858, which is a continuation-in-part of copending Ser. No. 69,959, filed Sept. 4, 1970 now abandoned, entitled SUBSTITUTED PHENOXYBENZONITRILES AS HERBICIDES.

BACKGROUND OF THE INVENTION

1. Field of the Invention

This invention is directed to new compounds of substituted phenoxybenzonitriles and their use as pre- and pos-emergence herbicides.

2. Description of the Prior Art

In U.S. Pat. No. 3,322,525 there is disclosed a compound of the structure

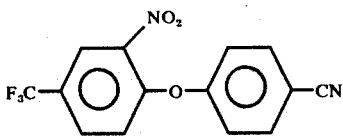

as a herbicide. France Pat. No. 1,502,538 discloses a compound of the structure

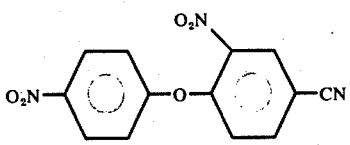

as a herbicide. Britain Pat. No. 951,651 discloses compounds of the structure

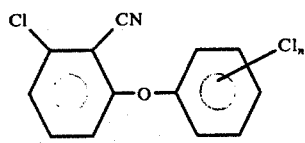

wherein if $n$ is 1, the chlorine is ortho or para, and if $n$ is 2, the chlorines are ortho and para, as herbicides.

Germany Pat. No. 1,912,600 discloses compounds of the structure

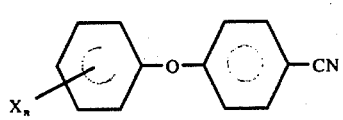

wherein X may be an alkyl group or halogen, as herbicides.

SUMMARY OF THE INVENTION

This invention provides compounds having the structural formula:

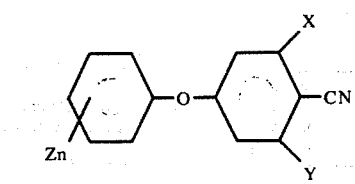

wherein X is hydrogen, halogen or alkyl, straight and branched chain alkyl, alkenyl, and cycloalkyl (e.g., $C_1$–$C_6$), Y is halogen (e.g., fluorine, chlorine, bromine and iodine) or lower alkyl (e.g., $C_1$–$C_6$), Z is halogen (e.g., fluorine, chlorine, bromine and iodine), and $n$ is an integer from 1 to 5; their use as herbicids; and herbicidally effective compositions containing at least one of the above compounds and a carrier therefor.

An important part of this invention is that X and/or Y may be alkyl. Compounds according to the invention which are alkyl-substituted are somewhat more herbicidally effective than their halogen counterparts. Applicant has no knowledge of such alkyl-substituted compounds in the prior herbicide art. Accordingly those compounds in which X and/or Y are alkyl are preferred embodiments of this invention.

DESCRIPTION OF SPECIFIC EMBODIMENTS

As will be noted from the formula, the compounds of the present invention are phenoxybenzonitriles, halo-substituted on the phenoxy ring and halo- or alkyl-substituted on the benzonitrile ring ortho to the para-cyano position. Mono-substituted compounds, i.e., compounds which are monohalo- or monoalkyl-substituted on the benzonitrile ring are highly advantageous. Examples of these compounds are 2-chloro-4-(2',4'-dichlorophenoxy)benzonitrile and 2-methyl-4-(2',4'-dichlorophenoxy)benzonitrile. The methyl-substituted compound being the more preferred for its alkyl-substitution on the benzonitrile ring.

Non-limiting examples of the compounds embodied for use in this invention include:

2-methyl-4-(2',4'-dichlorophenoxy)benzonitrile,
2-ethyl-4-(2',4'-dichlorophenoxy)benzonitrile,
2-propyl-4-(2',4'-dichlorophenoxy)benzonitrile,
2-amyl-4-(2',4'-dichlorophenoxy)benzonitrile,
2-hexyl-6-ethyl-(2'-chlorophenoxy)benzonitrile,
2-heptyl-4-(2',4'-dichlorophenoxy)benzonitrile,
2-isopropyl-4-(2',4'-dichlorophenoxy)benzonitrile,
2-sec-butyl-4-(2',4'-dichlorophenoxy)benzonitrile,
2-allyl-4-(2',4'-dichlorophenoxy)benzonitrile,
2-cyclopropylmethyl-4-(2',4'-dichlorophenoxy)benzonitrile,
2-chloro-4-(2',4'-dichlorophenoxy)benzonitrile,
2,6-dichloro-4-(2',4'-dichlorophenoxy)benzonitrile,
2-chloro-6-methyl-4-(2',4'-dichlorophenoxy)bezonitrile,
2-fluoro-4-(2',4'-dichlorophenoxy)benzonitrile,
2-chloro-4-(2',4',6'-trichlorophenoxy)benzonitrile,
2-methyl-4-(2'-chloro-4'-fluorophenoxy)benzonitrile,
2-chloro-4-(2',4'-difluorophenoxy)benzonitrile and the like.

The compounds of the present invention are highly effective as herbicides at high as well as low use concentrations as compared to similar compounds which are unsubstituted on the benzonitrile ring or if substituted thereon are not substituted ortho to the para-cyano position.

It is not known why ortho substitution with respect to a para positioned cyano group on the benzonitrile ring improves the effectiveness of these compounds, nonetheless their overall greater herbicidal activity is readily apparent in herbicidal screening tests. The compounds of this invention also retain substantially their high activity as herbicides at relatively low use concentrations, e.g., from about 1 to about 5 pounds per acre.

The compounds of this invention are readily prepared by the reaction of a suitable halogenated benzonitrile (e.g., 4-chloro-2-methylbenzonitrile) with a metal salt of 2,4-dichlorophenol in a suitable solvent, as in the following examples.

EXAMPLE 1

2-methyl-4-(2',4'-dichlorophenoxy)benzonitrile

A stirred solution of 4-chloro-2-methylbenzonitrile (7.85g., 0.05 mole) and the potassium salt of 2,4-dichlorophenol (10.07g., 0.05 mole) in 50 ml. of dimethyl acetamide was heated for 30 hours at 150° C. The cooled reaction mixture was diluted with 200 ml. of water to precipitate a brown oil. From this oil, an ether extract yielded 12.0g. of an oil. A vacuum distillation of the oil gave 8.6g. of 2-methyl-4-(2',4'-dichlorophenoxy)benzonitrile with a boiling point of 163°–166° C at 0.05 mm Hg. and a melting point of 52°–55° C.

EXAMPLE 2

2-methyl-4-(2'-chloro-4'-fluorophenoxy)benzonitrile

A stirred solution of 4-chloro-2-methylbenzonitrile (4.7g., 0.03 mole) and the potassium salt of 2-chloro-4-fluorophenol (5.54g., 0.03 mole) in 40 ml of dimethyl acetamide was heated for 48 hours at 150° C. The cooled reaction mixture was diluted with 200 ml. of water to precipitate a brown oil. An ether extract yielded 7.6g of 2-methyl-4-(2'-chloro-4'-fluorophenoxy)benzonitrile as a brown oil in about 90% purity.

EXAMPLE 3

2-chloro-4-(2',4'-dichlorophenoxy)benzonitrile

A stirred solution of 2,4-dichlorobenzonitrile (51.6g., 0.03 mole) and the potassium salt of 2,4-dichlorophenol (60.3g., 0.03 mole) in 250 ml. of dimethyl acetamide was heated for 24 hours at 120° C. The cooled reaction mixture was diluted with 1000 ml. of water and the resultant oil was extracted with ether. Evaporation of the ether solution gave 88.0g. of brown oil. Analysis by v.p.c. showed a 2:1 mixture of the desired compound and the isomeric 4-chloro-2-(2',4'-dichlorophenoxy) benzonitrile. A series of fractional crystallizations from 60°–110° C petroleum ether gave the desired 2-chloro-4-(2',4'-dichlorophenoxy)benzonitrile with a melting point of 69°–74° C. The minor isometric by-product melted at 110°–113° C.

EXAMPLE 4

2-chloro-4-(2',4',6'-trichlorophenoxy)benzonitrile

A stirred solution of 2,4-dichlorobenzonitrile (5.16g., 0.03 mole) and the potassium salt of 2,4,6-trichlorophenol (7.06g., 0.03 mole) in 35 ml of dimethyl acetamide was heated for about 60 hours at 150° C. The cooled reaction mixture was diluted with 200 ml of water to precipitate a brown oil which was extracted with ether. The initial brown oil amounting to 8.4g. was dissolved in hot heptane. Upon cooling, a yellow solid was obtained. It was collected by filtration and dried to give 3.9g. of 2-chloro-4-(2',4',6'-trichlorophenoxy)-benzonitrile with a melting point of 108°–116° C.

In illustration of this invention, the embodiments 2-methyl-4-(2',4'-dichlorophenoxy)benzonitrile, 2-methyl-4-(2'-chloro-4'-fluorophenoxy)benzonitrile, 2-chloro-4-(2',4'-dichlorophenoxy)benzonitrile and 2-chloro-4-(2',4',6'-trichlorophenoxy)benzonitrile were subjected to tests for herbicidal activity as described hereinafter with the test results being set forth in the Tables following the test descriptions. For comparison purposes, the Tables include results obtained with similar compounds, i.e., 4-(2',4'-dichlorophenoxy)-benzonitrile which is unsubstituted on the cyano-bearing ring, 6-chloro-2-(2',4'-dichlorophenoxy) benzonitrile which has an ortho-cyano group, and 6-methyl-2-(2',4'-dichlorophenoxy)benzonitrile* which also has an ortho-cyano group. All three of these compounds, labelled respectively Examples 5–7, illustrate the improved retention of activity of the compounds embodied herein at lower use concentrations.

* specially synthesized by applicant in a manner similar to that of Examples 1 and 2.

HERBICIDE TESTING METHOD

The test species propagated for testing are:

| | |
|---|---|
| Crabgrass | Pigweed |
| Yellow Foxtail grass | Turnip |
| Johnson grass | Cotton |
| Barnyard grass | Corn |
| | Bean |

Each specie is planted individually in 3 inch plastic pots containing potting soil. Four seeds each of the corn, bean, and cotton are seeded to a depth equal to the diameter of the seed. The other species are surface seeded and sprinkle with screened soil in an amount sufficient to cover the seed. Immediately after planting, all pots are watered by sub-irrigation in greenhouse trays. Pots for the pre-emergence phase of testing are seeded 1 day before treatment.

Planting dates for the post-emergence phase of testing are varied so that all seedlings will reach the desired stage of development simultaneously. The proper stage of development for treatment in the post-emergence tests is as follows:

| | |
|---|---|
| Grasses: | 2 inches in height |
| Pigweed & Turnip: | 1 or 2 true leaves visible above cotyledons |
| Cotton: | first true leaf 1 inch in length; expanded cotyledons |
| Corn: | 3 to 4 inches in height |
| Bean: | Primary leaves expanded, growing point at primary leaf node. |

Spray applications are made in a hood containing a movable belt and fixed spray nozzle. For passage through the spray hood, one pot of each species (pre-emergence phase) is placed on the forward half of a wooden flat and one pot of established plants (post-emergence phase) is placed on the rear half of the flat. Treatments are moved to the greenhouse after spraying. Watering during the observation period is applied only by sub-irrigation.

Compounds are screened at rates of application equivalent to 8, 4 and 2 pounds actual/acre in a spray volume of 38 gal/acre. Spray hood constants required to deliver the above volume are as follows:

| | |
|---|---|
| Belt Speed: | 2 mph |
| Air Pressure: | adjusted to provide 38 gpa delivery |
| Nozzle Tip: | 8003E (provided uniform cross-section flat spray) |

Formulations for spray applications (as used in the compositions for which data are set forth in the Tables hereinafter) are prepared in 50 ml. volumes with the following components:

Eight Pounds per Acre Rate
1. 1.24 grams compound
2. 49 ml. acetone as solvent
3. 1 ml. xylene-Atlox 3414 (surface-active emulsifier)

Four Pounds per Acre Rate
1. 0.62 grams compound
2. 49 ml. acetone as solvent
3. 1 ml. xylene-Atlox 3414

Two Pounds per Acre Rate
1. 0.31 grams compound
2. 49 ml. acetone as solvent
3. 1 ml. xylene-Atlox 3414

Compounds that are insoluble in the customary solvents are formulated either in the Waring Blender and applied as suspensions with suitable carriers, or dispersants or prepared initially as wettable powders. Compounds that are not available in sufficient quantity for machine spraying are applied by hand with a De Vilbiss atomizer.

Two weeks after treatment, a pre- and post-emergence injury or control is visually rated as percent injury or control (precent effectiveness).

Foxtail grass and Barnyard grass, annual grass weeds which reproduce by seed and are problems in lawns and field crops. They also prove highly effective against Johnson grass, a perennial grass weed which reproduces by seed and underground rhizomes and is primarily a problem in field crops. Also, they prove to be effective against Pigweed, an annual broadleaf weed which reproduces by seed and is one of the most serious broadleaf weed problems in major agronomic crops.

The compounds of this invention exhibit considerable pre- and post-emergence herbicidal activity and are disclosed for use in various ways to achieve pre-emergence or post-emergence contact control of undesirable herbs. They can be applied as the toxic components in herbicidal compositions of the compound and toxic components in herbicidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers, and the like. A wide variety of liquid and solid carriers can be used in the herbicidal compositions. Non-limiting examples of liquid carriers include water, organic oils such as kerosene, light oils and medium oils, and vegetable oils such as cottonseed oil.

TABLE 1

HERBICIDAL ACTIVITY* OF THE PHENOXYBENZONITRILES OF THIS INVENTION

| Example Compound | Concentration lbs/acre | Crabgrass | Yellow Foxtail grass | Johnson grass | Barnyard grass | Pigweed | Turnip | Cotton | Corn | Bean |
|---|---|---|---|---|---|---|---|---|---|---|
| | | | Pre-Emergence Activity | | | | | | | |
| 1 | 8 | 100 | — | 100 | 100 | — | 0 | 30 | 0 | 80 |
| | 4 | 90 | 100 | 90 | 70 | 100 | 0 | 50 | 50 | 100 |
| | 2 | 90 | 80 | 90 | 40 | 100 | 20 | 0 | 20 | 50 |
| 2 | 10** | 90 | — | 90 | — | — | 0 | — | — | — |
| | 4 | 60 | — | 90 | 50 | — | 20 | 20 | 30 | 0 |
| 3 | 8 | 100 | — | — | — | — | 20 | — | — | 0 |
| | 4 | — | — | 90 | 80 | — | 20 | 50 | 30 | 50 |
| | 2 | 70 | 80 | 50 | 30 | 100 | 0 | 80 | 50 | 100 |
| 4 | 8 | 80 | 90 | 40 | 30 | — | 70 | 30 | 0 | 100 |
| | 2 | — | — | 40 | 30 | — | 20 | 0 | 20 | 0 |
| 5 | 8 | 100 | — | 100 | 90 | 100 | 0 | 30 | 0 | 100 |
| | 4 | 40 | — | 20 | 20 | 80 | 20 | 30 | 0 | 80 |
| 6 | 8 | 0 | — | 0 | 0 | 70 | 0 | 100 | 0 | 100 |
| 7 | 4 | 80 | — | 50 | 70 | 0 | 60 | 80 | 0 | 100 |

*Herbicidal activity is measured in percent effectiveness
**Formulations prepared according to method disclosed on page 9 - 1.55 grams of compound used

TABLE 2

HERBICIDAL ACTIVITY* OF THE PHENOXYBENZONITRILES OF THIS INVENTION

| Example Compound | Concentration lbs/acre | Crabgrass | Yellow Foxtail grass | Johnson grass | Barnyard grass | Pigweed | Turnip | Cotton | Corn | Bean |
|---|---|---|---|---|---|---|---|---|---|---|
| | | | Post-Emergence Activity | | | | | | | |
| 1 | 8 | 100 | — | 80 | 80 | — | 100 | 30 | 60 | 100 |
| | 4 | 60 | — | 50 | 40 | 100 | 70 | 90 | 60 | 100 |
| 2 | 10** | 40 | — | — | — | — | 80 | 20 | — | 40 |
| | 4 | 40 | — | — | — | — | 0 | 20 | — | 20 |
| 3 | 8 | 50 | — | — | — | — | 30 | 60 | 50 | 70 |
| 4 | 8 | 60 | — | 90 | — | 100 | 40 | 70 | 30 | 80 |
| | 2 | 80 | — | 90 | 40 | — | 60 | 70 | 30 | 90 |
| 5 | 8 | 90 | — | 90 | 80 | 80 | 80 | 60 | 20 | 100 |
| | 4 | 60 | — | 40 | 30 | 80 | 60 | 50 | 40 | 100 |
| 6 | 8 | 60 | — | 50 | 20 | 50 | 40 | 0 | 0 | 80 |
| 7 | 8 | 40 | — | 40 | 30 | — | 40 | 0 | 20 | 30 |

*Herbicidal activity is measured in percent effectiveness
**Formulations prepared according to method disclosed on page 9 - 1.55 grams of compound used From the data in this Table, it will be noted that the substituted phenoxybenzonitriles of this invention have a broad range of both pre- and post-emergence herbicidal activity. The specific embodiments of these compounds used for testing, those of examples 1, 2, 3 and 4 show high effectiveness against Crabgrass, Yellow Non-limiting examples of solid carriers include talc, bentonite, diatomaceous earth, pyrophyllite, fullers earth, gypsum, flours derived from cotton seeds, and nut shells and various natural and synthetic clays having a pH not exceeding about 9.5.

The amount of the compounds of this invention utilized in herbicidal compositions will vary rather widely. It depends to some extent upon the type of composition in which the material is being used, the nature of the condition to be controlled, and the method of application (i.e., spraying, dusting, etc.). In the ultimate herbicidal compositions, as applied in the field, herbicide concentrations as low as 0.0001 weight percent of the total composition can be used. In general, compositions, as applied, containing about 0.05 weight percent herbicide in either liquid or solid carrier give excellent results. In some cases, however, stronger dosages up to about 10 weight percent may be required.

In practice, herbicidal compositions are usually prepared in the form of concentrates, which are diluted in the field to the concentration desired for application. For example, the concentrate can be a wettable powder containing large amounts of a compound of this invention, a carrier (e.g., attapulgite or other clay) and wetting and dispersing agents. Such a powder can be diluted prior to application, by dispersing it in water to obtain a sprayable suspension containing the concentration of herbicide desired for application. Other concentrates can be solutions that can be later diluted, e g., with kerosine. Thus, it is within the contemplation of this invention to provide herbicidal compositions containing up to about 80 percent, by weight of the composition, of a herbicidal compound of this invention. Accordingly, depending upon whether it is ready for application or it is in concentrated form, the contemplated herbicidal compositions contain between about 0.0001 percent and about 80 percent, by weight of the composition, of a herbicidal compound of this invention, and a carrier, liquid or solid, as defined hereinabove.

Although the present invention has been described with preferred embodiments, it is to be understood that modifications and variations may be restored to without departing from the spirit and scope of this invention, as those skilled in the art will readily understand.

What is claimed is:

1. The method for combatting herbs that comprises contacting them pre-emergently with an herbicidally effective amount of a compound having the formula:

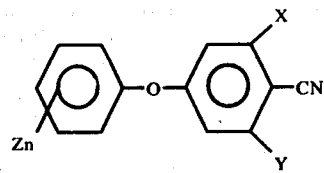

wherein X is hydrogen, Y is halogen or lower alkyl, Z is halogen and $n$ is an integer of from 1 to 3.

2. The method of claim 1, wherein said compound has the formula:

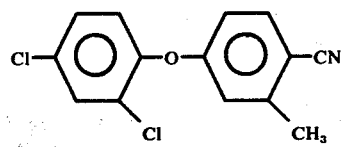

3. The method of claim 1, wherein said compound has the formula:

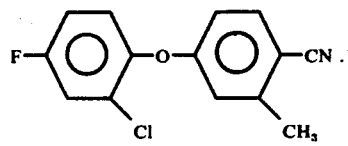

4. The method of claim 1, wherein said compound has the formula:

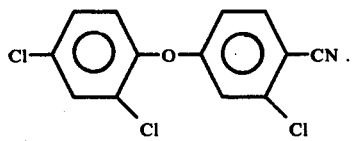

5. The method of claim 1, wherein said compound has the formula:

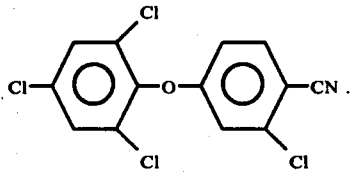

* * * * *

UNITED STATES PATENT AND TRADEMARK OFFICE
CERTIFICATE OF CORRECTION

PATENT NO. : 4,029,493
DATED : June 14, 1977
INVENTOR(S) : ROBERT JAMES THEISSEN It is certified that error appears in the above—identified patent and that said Letters Patent are hereby corrected as shown below:

| | |
|---|---|
| Column 1, lines 30 - 65 | The "inner circles" in the formulas are not clear. |
| Column 3, line 50 | "isometric" should be --isomeric--. |
| Column 4, line 31 | "sprinkle" should be --sprinkled--. |
| Column 7, line 50 | "pre-emergently" should be --pre-emergence--. |

Signed and Sealed this

Twenty-first Day of March 1978

[SEAL]

Attest:

RUTH C. MASON
Attesting Officer

LUTRELLE F. PARKER
Acting Commissioner of Patents and Trademarks